United States Patent

Oguchi et al.

(10) Patent No.: US 8,404,258 B2
(45) Date of Patent: Mar. 26, 2013

(54) EXTERNAL PREPARATION FOR THE SKIN

(75) Inventors: Nozomi Oguchi, Yokohama (JP); Reiji Miyahara, Yokohama (JP); Hiroyuki Kakoki, Yokohama (JP); Takashi Ohmori, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 636 days.

(21) Appl. No.: 12/074,394

(22) Filed: Mar. 4, 2008

(65) Prior Publication Data

US 2008/0293811 A1   Nov. 27, 2008

Related U.S. Application Data

(62) Division of application No. 10/490,616, filed on Mar. 25, 2004, now abandoned.

(30) Foreign Application Priority Data

Sep. 26, 2001 (JP) .................. 2001-293922

(51) Int. Cl.
*A61K 8/02* (2006.01)
*A01N 37/02* (2006.01)
(52) U.S. Cl. ........................ 424/401; 514/547
(58) Field of Classification Search .......................... None
See application file for complete search history.

(56) References Cited

U.S. PATENT DOCUMENTS 4,673,569 A * 6/1987 Shernov et al. ................. 424/47
2003/0091518 A1 * 5/2003 Pauly et al. ..................... 424/59

* cited by examiner

*Primary Examiner* — Lezah Roberts
*Assistant Examiner* — Nannette Holloman
(74) *Attorney, Agent, or Firm* — Andrew F. Young, Esq.; Lackenbach Siegel, LLP

(57) ABSTRACT

A skin treatment composition that characteristically contains alkylene polyglycol dineopentanoate having a specific structure.

The object is to provide a skin treatment composition that gives a refreshing sensation at the time of application and contains an oil component that is highly safe with low skin irritation.

The skin treatment composition specifically contains diethyleneglycol dineopentanoate, triethyleneglycol dineopentanoate, tetraethyleneglycol dineopentanoate, dipropyleneglycol dineopentanoate, tripropyleneglycol dineopentanoate, etc.

Dipropyleneglycol dineopentanoate and tripropyleneglycol dineopentanoate are particularly preferable in terms of the sensation at the time of application; they provide a skin treatment composition that is particularly superior in absorption into the skin and a sensation of permeation and highly safe.

2 Claims, No Drawings

EXTERNAL PREPARATION FOR THE SKIN

CROSS REFERENCE TO A RELATED APPLICATIONS

This is a divisional patent application of co-pending application Ser. No. 10/490,616, filed Mar. 25, 2004, which is now abandoned.

TECHNICAL FIELD

The present invention relates to a skin treatment composition that gives a refreshing sensation at the time of application and contains an oil component that is highly safe with low skin irritation.

BACKGROUND ART

Silicone oil has been added frequently to skin treatment compositions as an oil component that gives a refreshing sensation at the time of application.

However, since silicone oil has poor solubility with drugs and/or ultraviolet absorbents, hydrocarbon type oil components that give a refreshing sensation at the time of application have been desired.

However, an oil component that gives a refreshing sensation at the time of application has a small molecular weight and therefore a higher percutaneous absorption into the skin. As result, skin irritation such as tingling tends to become more pronounced.

In view of the aforementioned problem, the inventors conducted earnest research and discovered that a skin treatment composition that gives a refreshing sensation at the time of application and is highly safe with low skin irritation can be obtained by blending in a specific alkylene polyglycol dineopentanoate as an oil component, and thus completed the present invention.

The object of the present invention is to provide a skin treatment composition that has a particularly refreshing sensation at the time of application and is highly safe.

DISCLOSURE OF INVENTION

That is, the present invention provides a skin treatment composition that characteristically contains an alkylene polyglycol dineopentanoate represented by the following general formula (1):

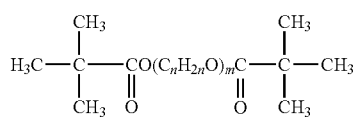

(In this formula, m denotes an integer 2-4, and n denotes an integer 2-3.)

Also, the present invention provides the aforementioned skin treatment composition wherein the compound represented by general formula (1) is tripropyleneglycol dineopentanoate represented by general formula (2):

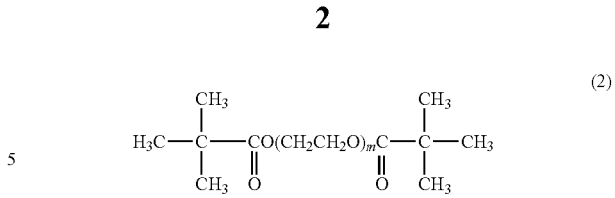

(In this formula, m denotes an integer 2-4.)

BEST MODE FOR CARRYING OUT THE INVENTION

The present invention is described in detail below.

The oil component of general formula (1) used in the present invention is a prior art hydrocarbon type oil component.

In the present invention, it is preferable to use a diester obtained by the condensation reaction between neopentyl chloride and polyethylene glycol.

The synthesis scheme is shown below:

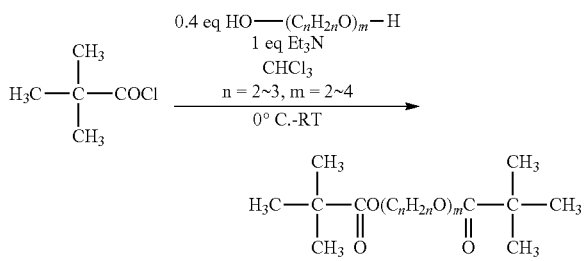

The reaction solution obtained by the aforementioned synthesis scheme is rinsed several times with an ammonium chloride aqueous solution and subjected to extraction with ethyl acetate; the extract solution is concentrated and roughly purified by column chromatography, and further purified by vacuum distillation.

(In general formula (1), m denotes an integer 2-4.) If m is 1, then the compound is volatile and malodorous. If m is five or more, the refreshing sensation at the time of application tends to be diminished.

Specific examples of alkylene polyglycol dineopentanoate that satisfies general formula (1) include diethyleneglycol dineopentanoate, triethyleneglycol dineopentanoate, tetraethyleneglycol dineopentanoate, dipropyleneglycol dineopentanoate, and tripropyleneglycol dineopentanoate.

Dipropyleneglycol dineopentanoate and tripropyleneglycol dineopentanoate are particularly preferable in terms of the sensation at the time of application; they provide a skin treatment composition that is particularly superior in terms of absorption into the skin and a sensation of permeation as well as being highly safe.

The blend ratio of the alkylene polyglycol dineopentanoate is not limited in particular. It is determined based on the formulation and the type of the product.

Usually, in the case of emulsified skin treatment compositions, the blend ratio is 0.001-50.0% (mass percentage), preferably 0.1-30.0% (mass percentage), of the total composition.

If it is less than 0.001%, then the effect of adding the oil component is not manifested; if it is more than 50.0%, then stickiness is felt after application.

The oil component of general formula (1) gives a refreshing sensation at the time of application, and is superior as an oil component to be blended into the base agent of skin treatment compositions such as cosmetics and quasi-drugs.

It is highly safe and superior in absorption into the skin as a hydrocarbon type oil component replacing silicone oil.

Also, drugs and ultraviolet absorbents can be easily blended in when the base agent contains the oil component of general formula (1).

The skin treatment composition of the present invention is prepared by blending the aforementioned oil component into an existing skin treatment composition base agent.

In addition to the aforementioned oil components, other ingredients used in skin treatment compositions can be blended as necessary in the skin treatment composition of the present invention; examples of such ingredients include powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water; and the skin treatment composition can be prepared for the target formulation with a conventional method.

Specific ingredients which can be blended in are listed below. The skin treatment composition of the present invention can be prepared by blending the aforementioned essential ingredients and any one, two or more of the following ingredients.

Examples of the powder ingredients include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, myristic acid zinc, calcium palmitate, and aluminum stearate), and boron nitride); organic powders (for example, polyamide resin powder (nylon powder), polyethylene powder, poly methyl methacrylate powder, polystyrene powder, powders of the copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low oxides of titanium); inorganic purple pigments (for example, manganese violet, cobalt violet); inorganic green pigments (for example, chromium oxide, chromium hydroxide, and cobalt titanate); inorganic blue pigments (for example, ultramarine blue and Berlin blue); pearl pigment (for example, titania coated mica, titania coated bismuth oxychloride, titania coated talc, coloration titania coated mica, bismuth oxychloride, fish scale flakes); metal powder pigments (for example, aluminium powder, copper powder); organic pigments such as Zr, barium or aluminium rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1; and natural colors (for example, chlorophyll and β-carotene).

Examples of the liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japan gimlet oil, jojoba oil, germ oil, and triglycerin.

Examples of the solid fats and oils include cacao butter, coconut oil, hydrogenated coconut oil, palm oil, palm kernel oil, Japanese core wax nucleus oil, hydrogenated oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Examples of the hydrocarbon oils include liquid petrolatum, ozocerite, squalane, pristane, paraffin, ceresin, squalene, petrolatum, and microcrystallin wax.

Examples of the higher fatty acids include lauric acid, myristic acid, palmitic acid, stearic acid, behenic acid, oleic acid, undecylenic acid, tall oil fatty acid, isostearic acid, linolic acid, linoleic acid, eicosapentaenoic acid (EPA), and docosahexanoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain ethyl alcohols (for example, mono stearyl glycerin ether (batyl alcohol), 2-decyltetradecynol, lanolin alcohol, cholesterol, phytosterol, hexyl dodecanol, iso stearyl alcohol, and octyl dodecanol).

Examples of the ester oils include isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, iso cetyl stearate, iso cetyl isostearate, cholesteryl hydroxy 12-stearate, di-2-ethylene glycol ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethylhexanoate, trimethylolpropane triisostearate, tetra-2-pentaerythritol ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyl decyl myristate, 2-hexyl decyl palmitate, 2-hexyl decyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, and various modified polysiloxanes (amino-modified polysiloxane, polyether-modified polysiloxane, alkyl-modified polysiloxane, and fluorine-modified polysiloxane).

Examples of the anionic surfactants include fatty acid soaps (for example, sodium laurate and sodium palmitate); higher alkyl sulfuric ester salts (for example, sodium lauryl sulfate and potassium laurylsulfate); alkylether sulfuric ester salts (for example, POE-triethanolamine laurylsulfate and sodium POE-lauryl sulfate); N-acyl sarcosinic acids (for example, sodium N-lauroyl sarcosinate); higher fatty acid ester sulfates (for example, hydrogenated coconut oil aliphatic acid glycerin sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkylether carboxylic acid; POE-alkylarylether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

Examples of the cationic surfactants include alkyltrimethylammonium salts (for example, stearyltrimethyl ammonium chloride and lauryltrimethyl ammonium chloride)alkylpyridinium salts (for example, cetylpyridinium chloride), distearyldimethylammonium chloride dialkyldimethylammonium salt; poly(N,N'-dimethyl-3,5-methylene piperidinium) chloride; alkyl quaternary ammonium salts; alkyl dimethylbenzyl ammonium salts; alkyl isoquinolinium salts; dialkylmorpholine salts; POE alkyl amines; alkyl amine salts; polyamine fatty acid derivatives; amylalcohol fatty acid derivatives; benzalkonium chloride; and benzethonium chloride.

Examples of the ampholytic surfactants include: imidazoline type ampholytic surfactants (for example, 2-undecyl-N, N,N-(hydroxyethyl carboxymethyl)-2-imidazoline sodium salt and 2-coco yl-2-imidazolinium hydroxide-1-carboxyethyloxy 2 sodium salt); and betaine type surfactants (for example, 2-heptadecyl-n-carboxymethyl-n-hydroxyethyl imidazolinium betaine, lauryldimethylaminoacetic acid betaine, alkyl betaine, amide betaine, and sulfobetaine).

Examples of the lipophilic nonionic surface active agent include sorbitan fatty acid esters (for example, sorbitan mono oleate, sorbitan mono isostearate, sorbitan mono laurate, sorbitan mono palmitate, sorbitan mono stearate, sorbitan sesquioleate, sorbitan trioleate, diglycerol sorbitan penta-2-ethylhexylate, diglycerol sorbitan tetra-2-ethylhexylate); glycerin polyglycerin aliphatic acids (for example, monocottonseed oil fatty acid glycerin, glyceryl monoerucate, glycerin sesquioleate, glyceryl monostearate, α,α'-glyceryl oleate pyroglutamate, glyceryl mono stearate mono malate); propylene glycol fatty acid esters (for example, propylene glycol monostearate) hydrogenated castor oil derivatives; and glycerin alkylethers.

Examples of the hydrophilic nonionic surface active agents include: POE-sorbitan fatty acid esters (for example, POE-sorbitan monooleate, POE-sorbitan monostearate, POE-sorbitan monoolate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glycerin fatty acid esters (for example, POE-monooleates such as POE-glycerin monostearate, POE-glycerin monoisostearate, and POE-glycerin triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE-2-octyl dodecyl ether, and POE-cholestanol ether); POE/POP-alkylethers (for example, POE/POP-cetyl ether, POE/POP-2-decyl tetradecyl ether, POE/POP-monobutyl ether, POE/POP-lanolin hydrate, and POE/POP-glycerin ether); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax/lanolin derivatives (for example, POE-sorbitol beeswax); alkanol amides (for example, coconut fatty acid diethanol amide, lauric acid monoethanol amide, and aliphatic acid isopropanol amide); POE-propylene glycol fatty acid esters; POE-alkyl amine; POE-fatty acid amide; sucrose fatty acid ester; alkyl ethoxy dimethylamine oxides; and trioleyl phosphoric acid.

Examples of the humectant include polyethylene glycol, propylene glycol, glycerin, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose fruit extract, yarrow extract, and sweet clover extract.

Examples of the natural water-soluble polymer include: plant-type polymers (for example, gum arabic, gum tragacanth, galactan, guar gum, carob gum, karaya gum, carrageenan, pectin, agar, quince seed (*Cydonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of the semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymethylcellulose, sodium carboxymethyl cellulose, crystal cellulose, and cellulose powder); and alginic acid-type polymers (for example, sodium alginate and propyleneglycol alginate).

Examples of the synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, a copolymer of polyethylene glycol 20,000, 40,000, or 60,000 and polyoxyethylene polyoxypropylene); acrylic polymers (for example, sodium polyacrylate, polyethylacrylate, and polyacrylamide); polyethyleneimine; and cationic polymers.

Examples of the thickeners include: gum arabic, carrageenan, karaya gum, gum tragacanth, carob gum, quince seed (*Cydonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of the ultraviolet absorbents include the following.

(1) Benzoic Acid-Type Ultraviolet Absorbents

For example, paraminobenzoic acid (hereafter abbreviated as PABA), PABA monoglycerin ester, N, N-dipropoxy PABA ethyl ester, N,N-diethoxy PABA ethyl ester, N,N-dimethyl PABA ethyl ester, N, N-dimethyl PABA butyl ester, and N,N-dimethyl PABA ethyl ester.

(2) Anthranilic Acid-Type Ultraviolet Absorbents

For example, homo mentyl-N-acetyl anthranilate.

(3) Salicylic Acid-Type Ultraviolet Absorbents

For example, amyl salicylate, mentyl salicylate, homo mentyl salicylate, octyl salicylate, phenyl salicylate, benzil salicylate, and p-isopropanol phenyl salicylate.

(4) Cinnamic Acid-Type Ultraviolet Absorbents

For example, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethyl hexanoyl-diparamethoxy cinnamate.

(5) Triazine-Type Ultraviolet Absorbents

For example, bisresorsinyl triazine.

More specifically,
bis{[4-(2-ethylhexyloxy)-2-hydroxy]phenyl}-6-(4-methoxyphenyl)1,3,5-triazine,
2,4,6-tris{4-(20ethylhexyloxycarbonyl)anilino}1,3,5-triazine, etc.

(6) Other Ultraviolet Absorbents

For example, 3-(4'-methylbenzylidene)-d,l-camphor, 3-benzylidene-d, 1-camphor, 2-phenyl-5-methyl benzoxazol, 2-(2'-hydroxy-5'-methylphenyl)benzotriazol, 2-(2'-hydroxy-5'-t-octylphenyl)benzotriazol, 2-(2'-hydroxy-5'-methylphenyl benzotriazol, dibenzaladine, dianisoylmethane, and 4-methoxy-4'-t-butyl dibenzoyl-methane, 5-(3,3-dimethyl-2-norbornylidene)-3-pentane-2-one. Pyridazinone derivatives such as dimorpholino pyridazine.

Examples of the sequestering agents include: 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of the lower alcohols include ethanol, propanol, isopropanol, isobutanol, and t-butyl alcohol.

Examples of the polyhydric alcohols include: dihydric alcohols (for example, ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, pentaerythritol such as 1,2,6-hexanetriol) pentahydric alcohols (for example, xylitol); hexahydric alcohols (for example, sorbitol, mannitol); polyhydric alcohol polymers (for example, diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycolmonomethyl ether acetate, propylene glycol monoethyl ether acetate, propylene glycol monopropyl ether acetate, and propylene glycol monophenyl ether acetate); glycerin mono alkyl ethers (for example, xylyl alcohol, selachyl alcohol, and batyl alcohol); sugar alcohols (for example, sorbitol, maltitol, maltotriose, mannitol, sucrose, erythritol, glucose, fructose, starch amylolysis sugar, maltose, xylitose, and alcohol prepared by the reduction of starch amylolysis sugar); glysolid; tetrahydro furfuryl alcohol; POE-tetrahydro furfuryl alcohol; POP-butyl ether; POP.POE-butyl ether; tripolyoxypropylene glycerin ether; POP-glycerin ether, POP-glycerin ether phosphoric acid; POP/POE-pentane erythritol ether, and polyglycerin.

Examples of the monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of the oligosaccharides include sucrose, umbelliferose, lactose, planteose, isolignoses, α,α-trehalose, raffinose, lignoses, umbilicine, stachyose and verbascose.

Examples of the polysaccharides include cellulose, quince seed, chondroitin sulfate, starch, galactan, dermatan sulfate, glycogen, gum arabic, heparan sulfate, hyaluronic acid, traganth gum, keratan sulfate, chondroitin, xanthan gum, mucoitin sulfuric acid, guar gum, dextran, kerato sulfate, locustbean gum, succinoglucane, and charonic acid.

Examples of the amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, acyl β-alanine sodium, glutathione, and pyrrolidone carboxylic acid.

Examples of the organic amines include monoethanolamine, diethanolamine, triethanolamine, morpholine, triisopropanolamine, 2-amino-2-carbinyl-1,3-propanediol, and 2-amino-2-carbinyl-1-propanol.

Examples of the high polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of the pH adjustment agents include buffers such as lactic acid-sodium lactate, citric acid-sodium citrate, and succinic acid-sodium succinate.

Examples of the vitamins include vitamins A, B1, B2, B6, C and E as well as their derivatives, pantothenic acid and its derivatives, and biotin.

Examples of the antioxidants include tocopherols, dibutyl hydroxytoluene, butyl hydroxyanisole, and gallic ester.

Examples of the antioxidation auxiliary agents include phosphoric acid, citric acid, ascorbic acid, maleic acid, malonic acid, succinic acid, fumaric acid, cephalin, hexameta phosphate, phytic acid, and ethylene diamine tetraacetic acid.

Examples of other possible ingredients include antiseptics (methylparaben, ethylparaben, butylparaben, and phenoxyethanol); anti-inflammatory agents (for example, glycyrrhizic acid derivatives, glycyrrhetinic acid derivatives, salicylic acid derivatives, hinokitiol, zinc oxide, and allantoin); whitening agents (for example, creeping saxifrage extract and arbutin); various extracts (for example, Phellodendri Cortex, goldthread, lithospermum root, *Paeonia lactiflora, Swertia japonica*, Birch, sage, loquat, carrot, aloe, *Malva sylvestris*, Iris, grape, *Coix ma-yuen*, sponge gourd, lily, saffron, *Cnidium officinale*, sheng jiang, *Hypericum erectum*, Ononis, garlic, Guinea pepper, chen pi, *Ligusticum acutilobum*, and seaweed), activators (royal jelly, photosensitizer, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and β-orizanol); anti-seborrhea agents (for example, sulfur and thiantol); and antiinflammatory agents (for example, tranexamic acid, thiotaurine, and hypotaurine).

Any formulation can be used for the skin treatment composition of the present invention.

The product form of the skin treatment composition of the present invention is also arbitrary.

It can be used in lotions, emulsions, creams, facial cosmetics such as packs; makeup cosmetics such as foundations, lipsticks, eye shadow; body cosmetics; aroma cosmetics; skin cleaners such as makeup removers and body shampoos; and ointments.

A skin treatment composition having an ultraviolet absorbent or various drugs is also preferable.

EXAMPLES

The present invention is described in detail below by referring to Examples. The present invention is not limited to them.

The blend ratios are in mass-percentage (%) units unless specified otherwise.

First, the test method and evaluation method used in Examples and Comparative examples are described below.

"Test Method Using Patch Test"

The test was conducted using a Finn Chamber (8 mm in diameter) with 24 hour-occlusion.

Test subjects were 46 male and female healthy volunteers (33 males and 13 females) whose ages range from 22 to 59 (average 42); 0.03 ml of the original specimen of alkylene polyglycol dineopentanoate was applied on the bent side of the forearm of the test subjects for 24 hours. The application site was secured with an elastic bandage; three hours after the removal of the bandage and the adhesive plaster the first evaluation (after-24-hours evaluation) was conducted according to the evaluation criteria of Table 1, and 24 hours later another evaluation (after-48-hours evaluation) was conducted with the same criteria.

TABLE 1

Evaluation criteria of the patch test

| Degree of skin reaction | Evaluation |
| --- | --- |
| No reaction | −: Negative |
| Mild erythema | ±: Equivocal |
| Erythema | +: Weakly positive |
| Erythema + edema | ++: Moderately positive |
| Erythema + edema + papule + serous papule + small blister | +++: Strongly positive |
| Large blister | ++++: Strongest positive |

"Evaluation (1): Refreshing Sensation on the Skin"

The refreshing sensation on the skin during use was evaluated with actual use test by ten specialized panelists. The evaluation criteria are as follows:

⊚ . . . Eight or more specialized panelists reported a refreshing sensation on the skin during use.

○ . . . Six or more and less than eight specialized panelists reported a refreshing sensation on the skin during use.

Δ . . . Three or more and less than six specialized panelists reported a refreshing sensation on the skin during use.

X . . . Less than three specialized panelists reported a refreshing sensation on the skin during use.

"Evaluation (2): Permeating Sensation on the Skin"

The permeating sensation on the skin during use was evaluated with actual use test by ten specialized panelists. The evaluation criteria are as follows:

⊚ . . . Eight or more specialized panelists reported a permeating sensation on the skin during use.

○ . . . Six or more and less than eight specialized panelists reported a permeating sensation on the skin during use.

Δ . . . Three or more and less than six specialized panelists reported a permeating sensation on the skin during use.

X . . . Less than three specialized panelists reported a permeating sensation on the skin during use.

"Evaluation (3): Non-Stickiness on the Skin"

The non-stickiness on the skin during use was evaluated with actual use test by ten specialized panelists. The evaluation criteria are as follows:

⊚ . . . Eight or more specialized panelists reported non-stickiness on the skin during use.

○ . . . Six or more and less than eight specialized panelists reported non-stickiness on the skin during use.

Δ . . . Three or more and less than six specialized panelists reported non-stickiness on the skin during X . . . Less than three specialized panelists reported non-stickiness on the skin during use.

Examples 1-12, Comparative Examples 1-6

The positive patch test ratio was measured for Examples 1-3 and Comparative examples 1-3. Skin treatment compositions (emulsions) of Examples 4-12 and Comparative examples 4-6 having the blend compositions listed in Table 3, Table 4, and Table 5 were prepared with a conventional method and the evaluation test was conducted for the aforementioned evaluations (1), (2), and (3). The results are shown in the tables.

The alkylene polyglycol dineopentanoate used here was prepared as follows: using the synthesis scheme described below, neopentyl chloride and polyethylene glycol were reacted for six hours at 0° C. to room temperature, HCl was removed, and a diester form was prepared by means of a condensation reaction.

The polyethylene glycols used here are diethylene glycol, triethylene glycol, tetraethylene glycol, dipropylene glycol, and tripropylene glycol.

The reaction solution was rinsed several times with an ammonium chloride aqueous solution and subjected to extraction with ethyl acetate; the extract solution was concentrated and roughly purified by column chromatography, and further purified by vacuum distillation. The purity of the preparation for use was 99% or higher.

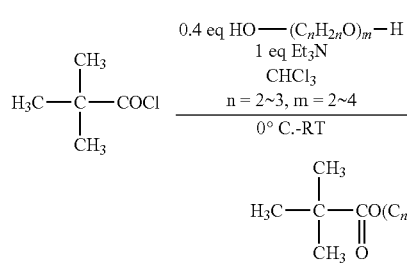

Results of the 24 hour-occlusion patch test for the original specimen of alkylene polyglycol dineopentanoate

TABLE 2

|  |  | Samples | Number (persons) | Evaluation time (hrs) | Positive ++++ | +++ | ++ | + | Equivocal ± | Negative − | Positive ratio (%) |
|---|---|---|---|---|---|---|---|---|---|---|---|
| Examples | 1 | Tripropyleneglycol dineopentanoate | 46 | 24 | 0 | 0 | 0 | 0 | 0 | 46 | 0 |
|  |  |  |  | 48 | 0 | 0 | 0 | 0 | 0 | 46 | 0 |
|  | 2 | Dipropyleneglycol dineopentanoate | 46 | 24 | 0 | 0 | 0 | 0 | 0 | 46 | 0 |
|  |  |  |  | 48 | 0 | 0 | 0 | 0 | 0 | 46 | 0 |
|  | 3 | Tetrapropyleneglycol dineopentanoate | 46 | 24 | 0 | 0 | 0 | 0 | 0 | 46 | 0 |
|  |  |  |  | 48 | 0 | 0 | 0 | 0 | 0 | 46 | 0 |
| Comparative example | 1 | Isocetyl oleate | 46 | 24 | 0 | 0 | 2 | 2 | 3 | 39 | 8.7 |
|  |  |  |  | 48 | 0 | 0 | 0 | 4 | 2 | 40 | 8.7 |
|  | 2 | Liquid petrolatum | 46 | 24 | 0 | 0 | 0 | 1 | 3 | 42 | 2.2 |
|  |  |  |  | 48 | 0 | 0 | 0 | 0 | 2 | 44 | 0 |
|  | 3 | Isononyl nonanoate | 46 | 24 | 0 | 1 | 4 | 5 | 5 | 31 | 22 |
|  |  |  |  | 48 | 0 | 0 | 5 | 4 | 5 | 32 | 20 |

Table 2 shows that alkylene polyglycol dineopentanoate exhibits low irritation.

TABLE 3

|  | Examples | | | |
|---|---|---|---|---|
| Ingredients | 4 | 5 | 6 | 7 |
| Dineopentanoic acidtripropylene glycol | 0.001 | 0.1 | 1.0 | 5.0 |
| Sodium hexamethaphosphate | 0.01 | 0.01 | 0.01 | 0.01 |
| Trisodium edetate | 0.03 | 0.03 | 0.03 | 0.03 |
| 1,3-butylene glycol | 5 | 5 | 5 | 5 |
| Potassium hydroxide | 0.1 | 0.1 | 0.1 | 0.1 |
| Carboxyvinyl polymer | 0.1 | 0.1 | 0.1 | 0.1 |
| Phenoxy ethanol | 0.15 | 0.15 | 0.15 | 0.15 |
| Purified water | Balance | Balance | Balance | Balance |
| Evaluation (1): Refreshing sensation on the skin | ○ | ◎ | ◎ | ◎ |
| Evaluation (2): Permeating sensation on the skin | ○ | ◎ | ◎ | ◎ |
| Evaluation (3): Non-stickiness on the skin | ○ | ◎ | ◎ | ◎ |

TABLE 4

| | Examples | | | | |
|---|---|---|---|---|---|
| Ingredients | 8 | 9 | 10 | 11 | 12 |
| Tripropyleneglycol dineopentanoate | 5 | — | — | — | — |
| Dipropyleneglycol dineopentanoate | — | 5 | — | — | — |
| Tetraethyleneglycol dineopentanoate | — | — | 5 | — | — |
| Triethyleneglycol dineopentanoate | — | — | — | 5 | — |
| Diethyleneglycol dineopentanoate | — | — | — | — | 5 |
| Sodium hexamethaphosphate | 0.01 | 0.01 | 0.01 | 0.01 | 0.01 |
| Trisodium edetate | 0.03 | 0.03 | 0.03 | 0.03 | 0.03 |
| 1,3-butylene glycol | 5 | 5 | 5 | 5 | 5 |
| Potassium hydroxide | 0.1 | 0.1 | 0.1 | 0.1 | 0.1 |
| Carboxyvinyl polymer | 0.1 | 0.1 | 0.1 | 0.1 | 0.1 |
| Phenoxy ethanol | 0.15 | 0.15 | 0.15 | 0.15 | 0.15 |
| Purified water | Balance | Balance | Balance | Balance | Balance |
| Evaluation (1): Refreshing sensation on the skin | ◎ | ◎ | ◎ | ◎ | ◎ |
| Evaluation (2): Permeating sensation on the skin | ◎ | ◎ | ◎ | ◎ | ◎ |
| Evaluation (3): Non-stickiness on the skin | ◎ | ◎ | ◎ | ◎ | ◎ |

TABLE 5

| | Comparative example | | |
|---|---|---|---|
| Ingredients | 4 | 5 | 6 |
| Tripropyleneglycol dineopentanoate | — | — | — |
| Decamethyl cyclopentane siloxane | 5 | — | — |
| Isocetyl oleate | — | 5 | — |
| Liquid petrolatum | — | — | 5 |
| Sodium hexamethaphosphate | 0.01 | 0.01 | 0.01 |
| Trisodium edetate | 0.03 | 0.03 | 0.03 |
| 1,3-butylene glycol | 5 | 5 | 5 |
| Potassium hydroxide | 0.1 | 0.1 | 0.1 |
| Carboxyvinyl polymer | 0.1 | 0.1 | 0.1 |
| Phenoxy ethanol | 0.15 | 0.15 | 0.15 |
| Purified water | Balance | Balance | Balance |
| Evaluation (1): Refreshing sensation on the skin | ◎ | ◎ | ○ |
| Evaluation (2): Permeating sensation on the skin | ◎ | ◎ | Δ |
| Evaluation (3): Non-stickiness on the skin | ◎ | ◎ | ◎ |

Stability Test for Sunscreen Formulations Containing a Slightly Soluble Ultraviolet Absorbent The sunscreens listed in Table 6 were stored at 0° C. for two months and then observed with a microscope to ascertain the presence of precipitation of a slightly-soluble ultraviolet absorbent (2,4-bis{[4-(2-ethylhexyloxy)-2-hydroxy]phenyl}-6-(4-methoxyphenyl)1,3,5-triazine)).

TABLE 6

| Ingredients | Example 13 | Comparative example 7 |
|---|---|---|
| Tripropyleneglycol dineopentanoate | 25 | — |
| Decamethyl cyclopentane siloxane | — | 25 |
| 2-ethylhexyl-p-methoxycinnamate | 7 | 7 |
| 2,4-bis{[4-(2-ethylhexyloxy)-2-hydroxy]phenyl}-6-(4-methoxyphenyl)1,3,5-triazine | 3 | 3 |
| 1,3-butylene glycol | 5 | 5 |
| Alcohol | 5 | 5 |
| Polyethylene glycol dipolyhydroxy stearate | 2 | — |
| Dimeticone copolyol | — | 2 |
| Preservative | Appropriate amount | Appropriate amount |
| Purified water | Balance | Balance |
| Precipitation of crystals ※ | ○ | X |

※ ○: No precipitation observed, X: Precipitation observed

The results above show that the sunscreens (emulsions) containing the oil component of the present invention do not cause precipitation of a slightly soluble ultraviolet absorbent even when they are stored at low temperatures for a long period of time, indicating superior stability of the formulations.

The results above show that the skin treatment compositions (emulsions) of the present invention exhibit superior effects for all the evaluation items. Other Examples of the present invention are shown below.

Example 14

Cream

| A. Oil phase | |
|---|---|
| Stearic acid | 10.0 mass % |
| Stearyl alcohol | 4.0 |
| Butyl stearate | 8.0 |
| Glyceryl monostearate | 2.0 |
| Vitamin E acetate | 0.5 |
| Vitamin A palmitate | 0.1 |
| Tripropyleneglycol dineopentanoate | 5.0 |
| Macadamia nut oil | 1.0 |
| Tea seed oil | 3.0 |
| Perfume | 0.4 |
| Phenoxy ethanol | Appropriate amount |
| B. Water phase | |
| Glycerin | 4.0 |
| 1,2 pentane diol | 3.0 |
| Sodium hyaluronate | 1.0 |
| Potassium hydroxide | 2.0 |
| Magnesium ascorbate phosphate | 0.1 |
| L-arginine hydrochloride | 0.01 |
| Trisodium edetate | 0.05 |
| Purified water | Balance |

(Preparation Method and Evaluation)

Oil phase A and water phase B were each heated up to 70° C. to be dissolved completely. The A phase was added to the B phase, followed by emulsification by means of an emulsifier. The emulsion was cooled by a heat exchanger to obtain cream. The obtained cream exhibited superior smoothness, no stickiness, and sustained moisture retention.

Example 15

Cream

| A. Oil phase | |
|---|---|
| Cetanol | 4.0 mass % |
| Petrolatum | 7.0 |
| Isopropyl myristate | 8.0 |
| Squalane | 10.0 |
| Glyceryl monostearate | 2.2 |
| POE(20) sorbitan monostearate | 2.8 |
| Tripropyleneglycol dineopentanoate | 10.0 |
| Vitamin E nicotinate | 2.0 |
| Perfume | 0.3 |
| δ-tocopherol | 0.05 |
| Phenoxyethanol | 0.05 |
| B. Water phase | |
| Glycerin | 10.0 |
| Sodium hyaluronate | 0.02 |
| Dipropylene glycol | 4.0 |
| Sodium pyrrolidone carboxylate | 1.0 |
| Disodium edetate | 0.01 |
| Purified water | Balance |

(Preparation Method and Evaluation)

Cream was obtained in the same manner as in Example 11. The obtained cream exhibited superior smoothness, no stickiness, and sustained moisture retention.

Example 16

Foundation

| A. Oil phase | |
|---|---|
| Cetanol | 3.5 mass % |
| Deodorized lanolin | 4.0 |
| Jojoba oil | 5.0 |
| Petrolatum | 2.0 |
| Squalane | 6.0 |
| Glyceryl monostearate | 2.5 |
| POE(60) hydrogenated castor oil | 1.5 |
| POE(20) cetyl ether | 1.0 |
| Tripropyleneglycol dineopentanoate | 2.0 |
| Pyridoxine tripalmitate | 0.1 |
| Paraben | 0.1 |
| Perfume | 0.3 |
| B. Water phase | |
| Propylene glycol | 10.0 |
| Powder preparation | 12.0 |
| Trisodium ethylenediamine hydroxyethyl triacetate | 1.0 |
| Purified water | Balance |

(Preparation Method and Evaluation)

Foundation was obtained in the same manner as in Example 13. The obtained foundation had a superior refreshing sensation and permeating sensation.

Example 17

Sunscreen Emulsion

| A. Oil phase | |
| --- | --- |
| Volatile cyclic silicone | 26.5 mass % |
| Titanium dioxide fine particles | 10.0 |
| (Dextrin fatty acid ester-treated: 40 nm) | |
| Zinc oxide fine particles | 10.0 |
| (Dextrin fatty acid ester-treated: 60 nm) | |
| Talc (Dextrin fatty acid ester-treated) | 4.0 |
| Tripropyleneglycol dineopentanoate | 4.0 |
| Organically modified montmorillonite | 0.5 |
| Octylmethoxy cinnamate | 7.5 |
| Phenoxy ethanol | 0.1 |
| Perfume | Appropriate amount |
| B. Water phase | |
| Purified water | 26.5 |
| Dipropylene glycol | 7.0 |

(Preparation Method and Evaluation)

The oil phase and the water phase were each mixed and dissolved separately. Dispersion of titanium dioxide in the oil phase was thoroughly conducted, to which the water phase was added, and emulsification was performed using an homogenizer. The obtained sunscreen emulsion exhibited a superior refreshing sensation.

Example 18

Emulsion

| A. Oil phase | |
| --- | --- |
| Squalane | 5.0 mass % |
| Oleyl oleate | 3.0 |
| Petrolatum | 2.0 |
| Sorbitan sesquioleate | 0.8 |
| Polyoxyethylene oleyl ether (20EO) | 1.2 |
| Triethyleneglycol dineopentanoate | 2.0 |
| Tripropyleneglycol dineopentanoate | 2.0 |
| Evening primrose oil | 0.5 |
| Perfume | 0.3 |
| Phenoxy ethanol | 0.2 |
| B. Water phase | |
| 1,3-butylene glycol | 4.5 |
| Ethanol | 3.0 |
| Carboxyvinyl polymer | 0.2 |
| Potassium hydroxide | 0.1 |
| L-arginine L-aspartate | 0.01 |
| Trisodium edetate | 0.05 |
| Purified water | Balance |

(Preparation Method and Evaluation)

The oil phase and the water phase were each mixed and dissolved. The water phase was added to the oil phase, followed by emulsification by means of a homogenizer. The obtained emulsion exhibited superior smoothness, no stickiness, and sustained moisture retention.

Example 19

Lotion

| A. Alcohol phase | |
| --- | --- |
| Ethanol | 5.0 mass % |
| POE oleyl ether | 2.0 |
| Tripropyleneglycol dineopentanoate | 1.0 |
| 2-ethylhexyl-P-dimethylamino benzoate | 0.18 |
| Perfume | 0.05 |
| B. Water phase | |
| 1,3-butylene glycol | 9.5 |
| Sodium pyrrolidone carboxylate | 0.5 |
| Nicotinamide | 0.3 |
| Glycerin | 5.0 |
| Purified water | Balance |

(Preparation Method and Evaluation)

The alcohol phase A was added to the water phase B, followed by solubilization to obtain a lotion. The obtained lotion exhibited superior smoothness, no stickiness, and sustained moisture retention.

Example 20

Solid Powdery Foundation

| | |
| --- | --- |
| Silicone-treated sericite | 15 mass % |
| Silicone-treated mica | 20 |
| Silicone-treated synthetic mica | 10 |
| Silicone-treated talc | Balance |
| Zinc oxide | 2 |
| Methylsiloxane network polymer spherical powder | 4 |
| Boron nitride | 3 |
| Zinc myristate | 2 |
| Crushed liquid titanated mica | 3 |
| Silicone-treated titanium oxide | 10 |
| Silicone-treated iron oxide | 4 |
| Silicone-treated zinc oxide | 5 |
| Tripropyleneglycol dineopentanoate | 1 |
| Dimethyl polysiloxane | 4 |
| 2-ethylhexyl-p-methoxycinnamate | 3 |
| Polyoxyethylene/alkyl co-modified silicone | 1 |
| Sorbitan sesquiisostearate | 1 |
| Paraben | Appropriate amount |
| δ-tocopherol | Appropriate amount |
| Perfume | Appropriate amount |

(Preparation Method and Evaluation)

The powder components, the oil components, and the crushed liquid titanated mica in the recipe were dispersed/mixed in ethyl alcohol by using a sand grinder mill having 3 mm-diameter zirconia beads. After distilling ethyl alcohol, the mixture was crushed once with a pulverizer; it was then packed in a container (inner tray made of resin) and molded by means of a dry press with a prior art method to obtain solid powdery foundation. The obtained solid powdery foundation exhibited a superior refreshing sensation.

Example 21

Cleansing Oil

| | |
|---|---|
| Liquid petrolatum | 68 mass % |
| Dimethyl polysiloxane | 2 |
| Ethanol | 0.3 |
| Isostearic acid | 0.5 |
| Lauric acid | 0.1 |
| Cetyl 2-ethylhexanoate | 10 |
| Tripropyleneglycol dineopentanoate | 5.0 |
| PEG-12 diisostearate | 4 |
| PEG-8 diisostearate | 1 |
| Coconut fatty acid diethanol amide | 0.1 |
| PEG-10 diisostearate | 3 |
| Tetrakis (2-hydroxyisopropyl) ethylenediamine | 0.1 |
| Vitamin E | 0.1 |
| Purified water | Balance |

(Preparation Method and Evaluation)

The cleansing oil was obtained by mixing and dissolving. The obtained cleansing oil exhibited superior smoothness, no stickiness, and sustained moisture retention.

Example 22

Hair Shampoo

| | |
|---|---|
| Polyoxyethylene laurylsulfate triethanolamine salt | 10.0 |
| Lauric acid diethanol amide | 5.0 |
| Lauryldimethylaminoacetic acid betaine | 5.0 |
| Ethylene glycol distearate | 3.0 |
| Propylene glycol | 2.0 |
| Sodium benzoate | 0.5 |
| Tripropyleneglycol dineopentanoate | 2.0 |
| Coloring agent | Appropriate amount |
| Perfume | Appropriate amount |
| Purified water | Balance |

(Preparation Method and Evaluation)

The aforementioned components were mixed with a conventional method to prepare a hair shampoo having a pearly look. Head hair washed with the obtained hair shampoo exhibited no stickiness and was nicely smooth even without the use of a conventional hair rinse after washing the hair.

Example 23

Hair Shampoo

| | |
|---|---|
| Sodium polyoxyethylene (EO average 3 moles) lauryl ether sulfate | 10.0 |
| Sodium cocoyl propyldimethyl glycine | 7.0 |
| Tripropyleneglycol dineopentanoate | 5.0 |
| Cationated cellulose ether | 3.0 |
| Coloring agent | Appropriate amount |
| Perfume | Appropriate amount |
| Purified water | Balance |

(Preparation Method and Evaluation)

The aforementioned components were mixed with a conventional method to prepare a clear hair shampoo. Head hair washed with the obtained hair shampoo exhibited no stickiness and was nicely smooth even without the use of a conventional hair rinse after washing the hair.

Example 24

Hair Shampoo

| | |
|---|---|
| Sodium dodecane-1,2-diol acetate ether | 10.0 mass % |
| Lauric acid diethanol amide | 5.0 |
| Sodium N-lauroyl-N'-carboxymethyl-N7-(2-hydroxyethyl) ethylenediamine | 8.0 |
| Ethylene glycol distearate | 3.0 |
| Propylene glycol | 2.0 |
| Sodium benzoate | 0.5 |
| Tripropyleneglycol dineopentanoate | 2.0 |
| Coloring agent | Appropriate amount |
| Perfume | Appropriate amount |
| Purified water | Balance |

(Preparation Method and Evaluation)

The aforementioned components were mixed with a conventional method to prepare a hair shampoo having a pearly look. Head hair washed with the obtained hair shampoo was superior in terms of tactile sensation of the hair during and after use, especially in terms of smoothness, and it was a hair cleaning agent that exhibited good foaming and cleansing effects even if a styling agent had been applied on the hair.

Example 25

Hair Shampoo

| | |
|---|---|
| Sodium dodecane-1,2-diol acetate ether | 10.0 mass % |
| Sodium N-lauroyl-N'-carboxymethyl-N'-(2-hydroxyethyl) ethylenediamine | 8.0 |
| Tripropyleneglycol dineopentanoate | 5.0 |
| Cationated cellulose ether | 3.0 |
| Coloring agent | Appropriate amount |
| Perfume | Appropriate amount |
| Purified water | Balance |

(Preparation Method and Evaluation)

The aforementioned components were mixed with a conventional method to prepare a clear hair shampoo. Head hair washed with the obtained hair shampoo was superior in tactile sensation of the hair during and after use, especially in terms of smoothness, and it was a hair cleaning agent that exhibited good foaming and cleansing effects even if a styling agent had been applied on the hair.

Example 26

Hair Rinse

| | |
|---|---|
| Cetyltrimethyl ammonium chloride | 0.6 mass % |
| Cetostearyl alcohol (C16/C18 = 6/4) | 4.0 |
| Dimethyl polysiloxane (5 cs) | 3.0 |
| Glyceryl monostearate | 1.0 |

-continued

| | |
|---|---|
| Liquid petrolatum | 3.0 |
| Tripropyleneglycol dineopentanoate | 8.0 |
| Glycerol monostearate | 1.0 |
| Glycerin | 5.0 |
| Propylene glycol | 5.0 |
| Preservative | Appropriate amount |
| Coloring agent | Appropriate amount |
| Perfume | Appropriate amount |
| Purified water | Balance |

(Evaluation)

This hair rinse gave a moist texture to the hair without stickiness, and improvesed the smooth and supple texture, thus giving superior sensation during use.

Example 27

Hair Treatment Cream

| | |
|---|---|
| Behenlytrimethyl ammonium chloride | 3.0 mass % |
| Cetostearyl alcohol (C16/C18 = 6/4) | 6.5 |
| Behenyl alcohol | 2.0 |
| Dimethyl polysiloxane (20 cs) | 3.0 |
| 2-octyldodecanol | 2.0 |
| Polyoxyethylene hydrogenated castor oil derivative | 0.3 |
| (Ethylene oxide 60 mole adduct) | |
| Polyoxyethylene stearyl ether | 1.0 |
| (Ethylene oxide 4 mole adduct) | |
| Soy lecithin | 0.5 |
| Liquid petrolatum | 3.0 |
| Tripropyleneglycol dineopentanoate | 5.0 |
| Glycerin | 10.0 |
| Dipropylene glycol | 5.0 |
| Preservative | Appropriate amount |
| Coloring agent | Appropriate amount |
| Perfume | Appropriate amount |
| Purified water | Balance |

(Evaluation)

This hair treatment cream gave moist texture to the hair without stickiness, and improved the smooth and supple texture, thus giving superior sensation during use.

Example 28

Hair Rinse

| | |
|---|---|
| Stearic acid diethylaminoethyl amide | 0.6 mass % |
| Cetyl alcohol | 2.0 |
| Stearyl alcohol | 1.0 |
| Dimethyl polysiloxane (5 cs) | 3.0 |
| Glycerol monostearate | 1.0 |
| Liquid petrolatum | 3.0 |
| Tripropyleneglycol dineopentanoate | 8.0 |
| Glycerol monostearate | 1.0 |
| Glycerin | 5.0 |
| Propylene glycol | 5.0 |
| L-glutamic acid | 0.6 |
| Preservative | Appropriate amount |
| Coloring agent | Appropriate amount |
| Perfume | Appropriate amount |
| Purified water | Balance |

(Evaluation)

This hair rinse gave a moist texture to the hair without stickiness, and improved the smooth and supple texture, thus giving superior sensation during use.

Example 29

Hair Treatment Cream

| | |
|---|---|
| Stearic acid dimethylaminopropyl amide | 3.0 wt % |
| Cetyl alcohol | 6.5 |
| Behenyl alcohol | 2.0 |
| Stearic acid | 2.0 |
| Dimethyl polysiloxane (20 cs) | 3.0 |
| 2-octyldodecanol | 2.0 |
| Polyoxyethylene hydrogenated castor oil derivative | 0.3 |
| (Ethylene oxide 60 mole adduct) | |
| Polyoxyethylene stearyl ether | 1.0 |
| (Ethylene oxide 4 mole adduct) | |
| Liquid petrolatum | 3.0 |
| Tripropyleneglycol dineopentanoate | 5.0 |
| Glycerin | 10.0 |
| Dipropylene glycol | 5.0 |
| L-glutamic acid | 1.0 |
| Preservative | Appropriate amount |
| Coloring agent | Appropriate amount |
| Perfume | Appropriate amount |
| Purified water | Balance |

(Evaluation)

This hair treatment cream gives moist texture to the hair without stickiness, and improves the smooth and supple texture, thus giving superior sensation during use.

Example 30

Make Cleansing Gel

| | |
|---|---|
| Hydroxyethyl cellulose | 0.1 mass % |
| Carboxyvinyl polymer | 0.4 |
| Alkyl acrylate/methacrylate copolymer | 0.2 |
| Trisodium edetate | Appropriate amount |
| Coconut fatty acid diethanol amide | 0.1 |
| Polyethylene glycol monoisostearate | 0.5 |
| Tripropyleneglycol dineopentanoate | 5.0 |
| Potassium hydroxide | Appropriate amount |
| Alcohol | 5.0 |
| Polyoxyethylene hydrogenated castor | 0.3 |
| Preservative | Appropriate amount |
| Decamethylcyclopentasiloxane | 18.0 |
| Methylpolysiloxane | 3.0 |
| Perfume | Appropriate amount |
| Purified water | Balance |

(Preparation Method and Evaluation)

The aforementioned components were emulsified by an emulsifier with a conventional method to obtain a make cleansing gel. The obtained make cleansing gel was easy to rinse off, and exhibited superior effects in terms of usability, safety, and the cosmetic-removal effect.

Example 31

Make Cleansing Gel

| | |
|---|---|
| Hydroxyethyl cellulose | 0.05 mass % |
| Carboxyvinyl polymer | 0.45 |
| Alkyl acrylate/methacrylate copolymer | 0.1 |
| Trisodium edetate | Appropriate amount |
| Sodium methyl cocoyl taurate | 0.01 |
| Polyethylene glycol monoisostearate | 3.0 |
| Tripropyleneglycol dineopentanoate | 7.0 |
| Poly(sodium aspartate) liquid | Appropriate amount |
| Chamomille extract | Appropriate amount |
| Potassium hydroxide | Appropriate amount |
| Alcohol | 5.0 |
| Polyoxyethylene hydrogenated castor | 0.1 |
| Preservative | Appropriate amount |
| Decamethylcyclopentasiloxane | 18.0 |
| Methylpolysiloxane | 3.0 |
| Perfume | Appropriate amount |
| Purified water | Balance |

(Preparation Method and Evaluation)

The aforementioned components were emulsified by an emulsifier with a conventional method to obtain a make cleansing gel. The obtained make cleansing gel was easy to rinse off, and exhibited superior effects in terms of usability, safety, and the cosmetic-removal effect.

Example 32

Body Shampoo

| | |
|---|---|
| Hydroxypropylmethyl cellulose | 0.1 mass % |
| Glycerin | 10.0 |
| Dipropylene glycol | 5.0 |
| Triethanolamine laurate | 12.0 |
| Lauryldimethylaminoacetic acid betaine | 5.0 |
| Coconut fatty acid diethanol amide | 3.0 |
| Tripropyleneglycol dineopentanoate | 5.0 |
| Chamomille extract | Appropriate amount |
| Trisodium edetate | Appropriate amount |
| Preservative | Appropriate amount |
| Coloring agent | Appropriate amount |
| Perfume | Appropriate amount |
| Purified water | Balance |

(Preparation Method and Evaluation)

The aforementioned components were stirred and dissolved with a conventional method, followed by cooling by a heat exchanger to obtain a body shampoo. The obtained body shampoo was easy to rinse off, and exhibited superior effects in terms of usability, safety, and the cosmetic-removal effect.

Example 33

Lipstick

| | |
|---|---|
| (1) Carnauba wax | 1.0 mass % |
| (2) Candelilla wax | 2.0 |
| (3) Ceresin | 10.0 |
| (4) Squalane | Balance |
| (5) Glyceryl triisooctanoate | 9.0 |
| (6) Glyceryl diisostearate | 13.0 |
| (7) Tripropyleneglycol dineopentanoate | 5.0 |
| (8) Silicone resin | 8.0 |
| (9) Hydroxypropyl-β-cyclodextrin | 1.0 |
| (10) Cholesteryl macadamiate | 3.5 |
| (11) Synthetic sodium magnesium silicate | 0.5 |
| (12) Hydrophobic silica | 0.5 |
| (13) Purified water | 2.0 |
| (14) Boron nitride | 10.0 |
| (15) Coloring agent | Appropriate amount |
| (16) Preservative | Appropriate amount |
| (17) Perfume | Appropriate amount |

(Preparation Method and Evaluation)

(11) and (12) were dispersed in (10), previously heated up to 60° C., and (9) and (13) were added to this mixture, followed by thorough stirring. This was added to separately heated and dissolved (1)-(8), followed by thorough stirring, and (14)-(17) were added, followed by dispersing and stirring; the product was then packed in a container to obtain a lipstick. The obtained lipstick was superior in terms of the sensation during use, and safety thereof.

INDUSTRIAL APPLICABILITY

The present invention can provide a skin treatment composition that gives a refreshing sensation at the time of application and contains an oil component that is highly safe with low skin irritation.

The invention claimed is:
1. A cosmetic composition for the skin comprising:
    (a) an oil phase comprising 1-25 wt % tripropyleneglycol dineopentanoate;
    (b) a water phase; and
    (c) one or more slightly soluble ultraviolet absorbents selected from the group consisting of paraminobenzoic acid (PABA), PABA mono glycerin ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, homo mentyl-N-acetyl anthranilate, amyl salicylate, mentyl salicylate, homo mentyl salicylate, octyl salicylate, phenyl salicylate, benzil salicylate, isopropanol phenyl salicylate, octyl cinnamate, ethyl-4-isopropyl cinnamate, methyl-2,5-diisopropyl cinnamate, ethyl-2,4-diisopropyl cinnamate, methyl-2.4-diisopropyl cinnamate, propyl-p-methoxy cinnamate, isopropyl-p-methoxy cinnamate, isoamyl-p-methoxy cinnamate, octyl-p-methoxycinnamate (2-ethylhexyl-p-methoxy cinnamate), 2-ethoxyethyl-p-methoxycinnamate, cyclohexyl-p-methoxy cinnamate, ethyl-alpha-cyano-beta-phenyl cinnamate, 2-ethylhexyl-alpha-cyano-beta-phenyl cinnamate, glyceryl mono-2-ethyl hexanoyldiparamethoxy cinnamate, bisresorsinyl triazine, bis{[4-(2-ethylhexyloxy)-2-hydroxy]phenyl}-6-(4-methoxyphenyl)1,3,5-triazine, 2,4,6-tris{4-(20ethylhexyloxycarbonyl)anilino}1,3,5-triazine, 3-(4'-methylbenzylidene)-d,l-camphor, 3-benzylidene-d,l-camphor, 2-phenyl-5-methyl benzoxazol, 2-(2'-hydroxy-5'-methylphenyl)benzotriazol, 2-(2'-hydroxy-5'-t-octylphenyl)benzotriazol, 2-(2'-hydroxy-5'-methylphenyl)benzotriazol, dibenzaladine, dianisoylmethane, 4-methoxy-4'-t-butyl dibenzoylmethane, 5-(3.3-dimethyl-2-norbornylidene)-3-pentane-2-one, and dimorpholino pyridazine, wherein the cosmetic composition is a cream, lotion, sunscreen emulsion, foundation powder, cleansing oil, cleansing gel, or make up remover.

2. A cosmetic composition for the skin of claim 1, further comprising one or more components selected from the group consisting of a powder, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water.

* * * * *

UNITED STATES PATENT AND TRADEMARK OFFICE
CERTIFICATE OF CORRECTION

PATENT NO. : 8,404,258 B2  
APPLICATION NO. : 12/074394  
DATED : March 26, 2013  
INVENTOR(S) : Oguchi et al.

Page 1 of 1

It is certified that error appears in the above-identified patent and that said Letters Patent is hereby corrected as shown below:

On the Title Page, insert Items:

--(86) PCT No.: PCT/JP0209755

§ 371 (c)(1),
(2), (4) Date: Sept. 24, 2002

(87) PCT Pub. No.: WO/2003/026698

PCT Pub. Date: April 3, 2003--

Signed and Sealed this
Fourth Day of June, 2013

Teresa Stanek Rea
*Acting Director of the United States Patent and Trademark Office*